(12) United States Patent
Miyasa

(10) Patent No.: US 11,705,237 B2
(45) Date of Patent: Jul. 18, 2023

(54) INFORMATION PROCESSING APPARATUS, METHOD FOR CONTROLLING INFORMATION PROCESSING APPARATUS, AND STORAGE MEDIUM

(71) Applicant: CANON KABUSHIKI KAISHA, Tokyo (JP)

(72) Inventor: Kazuhiro Miyasa, Chiba (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 49 days.

(21) Appl. No.: 17/066,291

(22) Filed: Oct. 8, 2020

(65) Prior Publication Data
US 2021/0042924 A1 Feb. 11, 2021

Related U.S. Application Data

(63) Continuation of application No. PCT/JP2019/015077, filed on Apr. 5, 2019.

(30) Foreign Application Priority Data

Apr. 12, 2018 (JP) ................. 2018-077139

(51) Int. Cl.
| | |
|---|---|
| *G06K 9/00* | (2022.01) |
| *G16H 30/20* | (2018.01) |
| *G16H 30/40* | (2018.01) |
| *G06T 7/00* | (2017.01) |
| *G06V 10/94* | (2022.01) |

(52) U.S. Cl.
CPC .......... *G06T 7/0014* (2013.01); *G06V 10/945* (2022.01); *G16H 30/20* (2018.01); *G16H 30/40* (2018.01)

(58) Field of Classification Search
CPC .............. G06T 7/0014; G06T 2200/24; G06T 2207/10072; G06T 1/00; G06T 7/0016; G06V 10/443; G06V 2201/03; G16H 30/20; G16H 30/40; G06K 9/6253; A61B 6/03

See application file for complete search history.

(56) References Cited

U.S. PATENT DOCUMENTS

| | | | |
|---|---|---|---|
| 2016/0253468 A1* | 9/2016 | Osawa | G16H 30/20 600/407 |
| 2017/0039322 A1* | 2/2017 | Reicher | G06F 16/583 |
| 2018/0049712 A1* | 2/2018 | Muraoka | A61B 6/461 |

FOREIGN PATENT DOCUMENTS

| | | |
|---|---|---|
| JP | 2000-152931 A | 6/2000 |
| JP | 2004-160103 A | 6/2004 |
| JP | 2005-051702 A | 2/2005 |
| JP | 2005-277558 A | 10/2005 |

(Continued)

*Primary Examiner* — Xin Jia
(74) *Attorney, Agent, or Firm* — Canon U.S.A., Inc. IP Division

(57) ABSTRACT

An information processing apparatus includes an acquisition unit, a determination unit, and an output unit. The acquisition unit acquires history information of image processing using a plurality of medical images. The determination unit determines, using the acquired history information, whether each of a plurality of candidate images that are candidates of a second medical image used for image processing together with a first medical image selected by an operator has already been processed. The output unit outputs a notification in accordance with the result of the determination.

19 Claims, 13 Drawing Sheets

(56) References Cited

FOREIGN PATENT DOCUMENTS

| | | |
|---|---|---|
| JP | 2006-312025 A | 11/2006 |
| JP | 2010-088709 A | 4/2010 |
| JP | 2013-126575 A | 6/2013 |
| JP | 2016-126477 A | 7/2016 |

* cited by examiner

FIG. 4

| HISTORY ID | REFERENCE IMAGE (SERIES ID) | COMPARISON IMAGE (SERIES ID) | PROCESSING PARAMETER (PARAMETER ID) | PROCESSING RESULT IMAGE (SERIES ID) |
|---|---|---|---|---|
| 001 | 0000001 | 0000002 | 01 | 1000001 |
| 002 | 0000010 | 0000020 | 01 | 1000002 |
| 003 | 0000123 | 0000456 | 02 | 1000003 |
| 004 | 0001234 | 0004567 | 03 | 1000004 |
| 005 | 0012345 | 0000010 | 02 | 1000005 |

INFORMATION PROCESSING APPARATUS, METHOD FOR CONTROLLING INFORMATION PROCESSING APPARATUS, AND STORAGE MEDIUM

CROSS-REFERENCE TO RELATED APPLICATIONS

This application is a Continuation of International Patent Application No. PCT/JP2019/015077, filed Apr. 5, 2019, which claims the benefit of Japanese Patent Application No. 2018-077139 filed Apr. 12, 2018, both of which are hereby incorporated by reference herein in their entirety.

BACKGROUND OF THE DISCLOSURE

Field of the Disclosure

The aspect of the embodiments relates to an information processing apparatus, a method for controlling the information processing apparatus, and a storage medium.

Background Art

In the medical field, doctors make diagnosis using medical images captured by a variety of modalities. For example, in order to monitor an object under examination over time, a doctor compares a plurality of images captured by the same modality at different times with one another to observe changes in the object over time. To assist a doctor in observing changes over time in an object, PTL 1 describes a technique to visualize a change in, for example, a lesion over time by presenting a subtraction image obtained by subtracting a comparison image from a reference image. As described above, a technique is disclosed that assist doctors in diagnosis by performing image processing on a combination of a plurality of images and presenting the result of image processing.

CITATION LIST

Patent Literature

PTL1: Japanese Patent Laid-Open No. 2013-126575

However, in the technique of PTL 1, unnecessary image processing may be performed again on an already processed combination of images, resulting in waste.

SUMMARY OF THE DISCLOSURE

According to the aspect of the embodiments, an information processing apparatus has the following configuration. That is, an information processing apparatus is including an acquisition unit configured to acquire history information of image processing using a plurality of medical images, a determination unit configured to determine, using the acquired history information, whether image processing has already been performed that is to be performed on each of a plurality of candidate images that are candidates of a second medical image used for the image processing together with a first medical image selected by an operator, and an output unit configured to output a notification in accordance with a result of the determination.

Further features of the disclosure will become apparent from the following description of exemplary embodiments with reference to the attached drawings.

BRIEF DESCRIPTION OF THE DRAWINGS

FIG. 4 is a diagram illustrating an example of the information in a history information list.

DESCRIPTION OF THE EMBODIMENTS

Exemplary embodiments of an information processing apparatus according to the disclosure is described in detail below with reference to the accompanying drawings. It should be noted that the scope of the disclosure is not limited to the illustrated examples.

First Embodiment

The information processing apparatus according to the present embodiment is an apparatus that presents information to a user (an operator) if image processing of a specified medical image has already been performed. More specifically, the image processing apparatus is the following operations. That is, upon performing image processing on a combination of a plurality of medical images, the information processing apparatus according to the present embodiment stores history information indicating that the combination of a plurality of medical images has undergone the image processing. Thereafter, if a user specifies one of the medical images for which history information has been stored (hereinafter referred to as a "first selection image"), the information processing apparatus displays information regarding already processed medical images in combination with the specified image distinctively from medical images that have not yet been processed. In this way, when the user specifies one medical image, they can get to know the already processed medical images in combination with the specified medical image. As a result, the probability can be reduced of regenerating an image already generated as the result of image processing by the user. Thus, waste can be eliminated. The configuration and processing according to the present embodiment are described below with reference to FIGS. 1 to 6 and FIG. 13.

Figure 1:
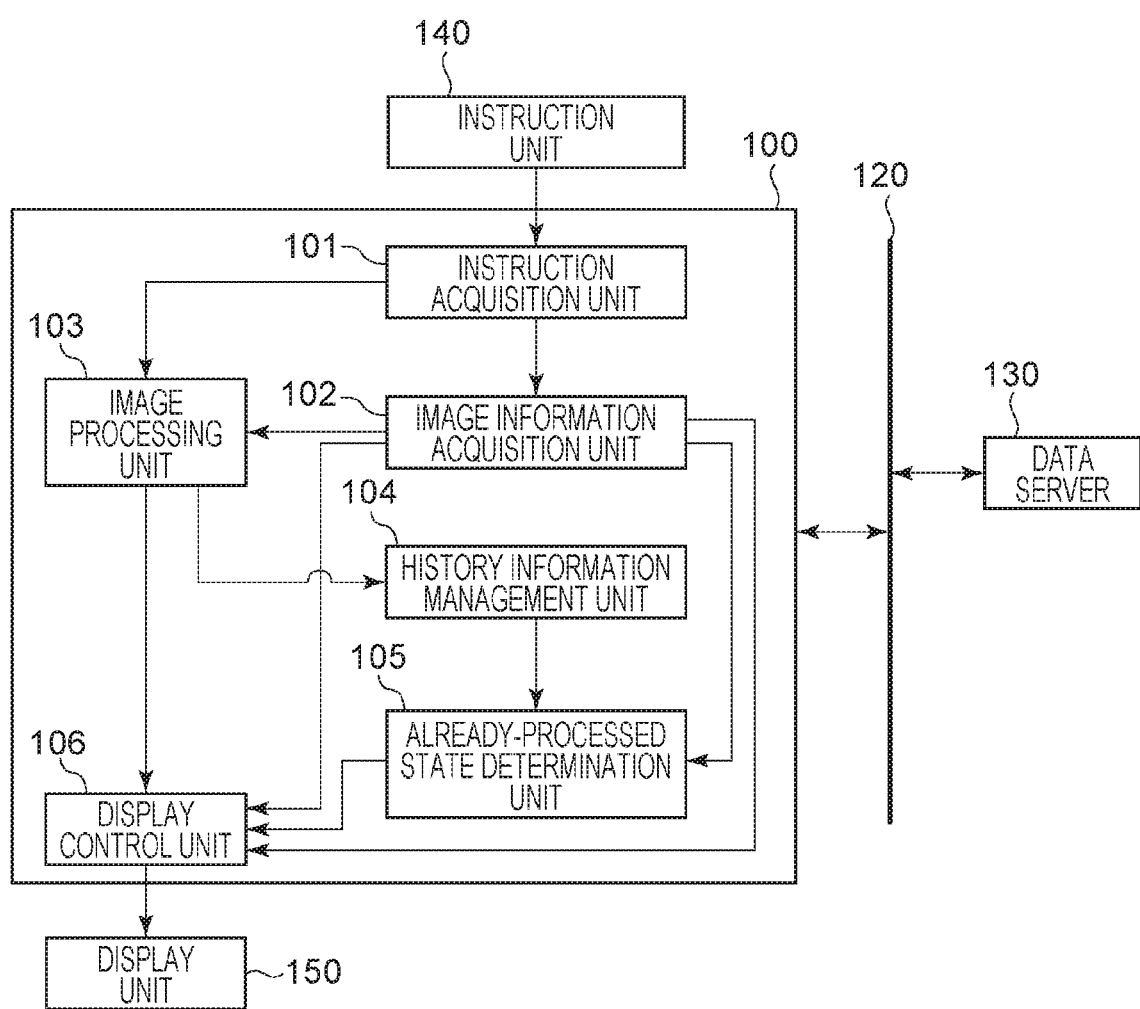
FIG. 1 illustrates the configuration of an information processing system according to a first embodiment.

FIG. 1 illustrates the configuration of an information processing system according to the present embodiment. As illustrated in FIG. 1, an information processing apparatus 100 according to the present embodiment is connected to a data server 130 via a network 120.

The data server 130 holds a plurality of medical images. The medical images held by the data server 130 are obtained by previously capturing the image of an object under examination under different conditions (e.g., different modalities, image capture modes, dates and times, and postures). The plurality of medical images may be two-dimensional images or three-dimensional tomographic images. If the medical images are two-dimensional images, the modality to capture the images may be a simple X-ray image capture device, a mammography image capture device, a fundus camera, or the like. If the medical images are three-dimensional tomographic images, the modality to capture the images may be an MRI apparatus, an X-ray CT apparatus, a three-dimensional ultrasonic image capturing apparatus, a photoacoustic tomography apparatus, a PET/SPECT, an OCT apparatus, for example. The medical images may be any images to be captured for generating the result of image processing. For example, the images may be captured by different modalities or different image capture modes at the same time. Alternatively, the images may be images obtained by capturing the images of the same patient having the same posture by the same modality at different dates and times for follow-up observation. Still alternatively, the images may be atlas images generated on the basis of clinical images of a plurality of patients or artificial images generated on the basis of computer simulation. Note that when the medical images are three-dimensional tomographic images, the medical images are three-dimensional images generated as a set of two-dimensional tomographic images. In this case, the position and posture of each of the two-dimensional tomographic images are converted into a reference coordinate system (a coordinate system in a space with the object under examination being as a reference) and are held by the data server 130. The medical images are input to the information processing apparatus 100 in accordance with an instruction from a user who operates an instruction unit 140.

The information held by the plurality of medical images is described below. The medical image holds incidental information in addition to the image data composed of pixel values. The incidental information represents various types of incidental information regarding the examination image. Examples of the incidental information include a patient ID, a patient name, an examination ID, an examination date, identification information (series ID) of a set of tomographic images, an image capture date, and a modality. The incidental information according to the present embodiment is recorded in a medical image as the header information of the medical image. The incidental information can be held as header information based on DICOM (Digital Imaging and Communication in Medicine), which is a widely used standard for the incidental information for medical images. Note that the incidental information is not limited thereto. Any information that includes identification information that can identify a specific medical image can be the incidental information. Also note that since the incidental information accompanies a medical image, it is assumed that when the data of a medical image is input or output, the incidental information is included in the medical image and is input or output together with the image data.

The information processing apparatus 100 is an apparatus that receives a processing request from a user via the instruction unit 140, performs information processing, and outputs the result of processing to a display unit 150. The information processing apparatus 100 functions as a terminal device operated by a user, such as a medical doctor, for interpretation of radiogram. The information processing apparatus 100 exchanges data with the data server 130 and requests the data server 130 to process the data. More specifically, upon receiving an instruction from the user via the instruction unit 140, the information processing apparatus 100 acquires, from the data server 130, a first selection image and a second selection image to be image-processed as a pair of images to be image-processed. Thereafter, the information processing apparatus 100 performs image processing on the combination of the first selection image and the second selection image and stores or outputs the result of image processing.

The hardware configuration of the information processing apparatus 100 is described below with reference to FIG. 13. The information processing apparatus 100 includes a control unit 1301, a ROM (Read Only Memory) 1302, a RAM (Random Access Memory) 1303, a storage unit 1304, a communication interface (communication IF) 1305, and a display control unit 106. These hardware units are connected to the system bus. In addition, the information processing apparatus 100 has the instruction unit 140 and the display unit 150 connected thereto. Only one instruction unit 140 and only one display unit 150 are sufficient. In addition, the information processing apparatus 100 is connected to the data server 130 via the communication IF 1305.

The control unit 1301 is, for example, a processor such as a CPU (Central Processing Unit). The control unit 1301 performs overall control of the hardware units connected to the system bus. The ROM 1302 is configured by a nonvolatile memory or the like and stores a variety of programs. The RAM 1303 is hardware that is configured by a volatile memory or the like. The RAM 1303 serves as a main memory, a work area, or the like of the control unit 1301 and temporarily stores various types of information as data. The storage unit 1304 is a storage device, such as an HDD (Hard Disk Drive) or SSD (Solid State Drive). The communication IF 1305 is, for example, a LAN (Local Area Network) card or the like. The communication IF 1305 enables communication between an external device (for example, a data server or the like) and the information processing apparatus 100 via a network. The display control unit 106 is a control unit that causes the display unit 150 to display various types of information. The display control unit 106 corresponds to, for example, a graphic controller (a GPU or the like). Note that the information processing apparatus 100 may have a configuration that does not include the display control unit 106. Instead, the control unit 1301 may have the function of the display control unit 106.

The variety of programs and the like used by the information processing apparatus 100 according to the disclosure to perform various processes (described below) are recorded in the storage unit 1304. The programs are loaded into the RAM 1303 and are executed by the control unit 1301 as needed. In addition, definition files and various information tables used by the programs according to the disclosure are stored in the storage unit 1304.

Figure 13:
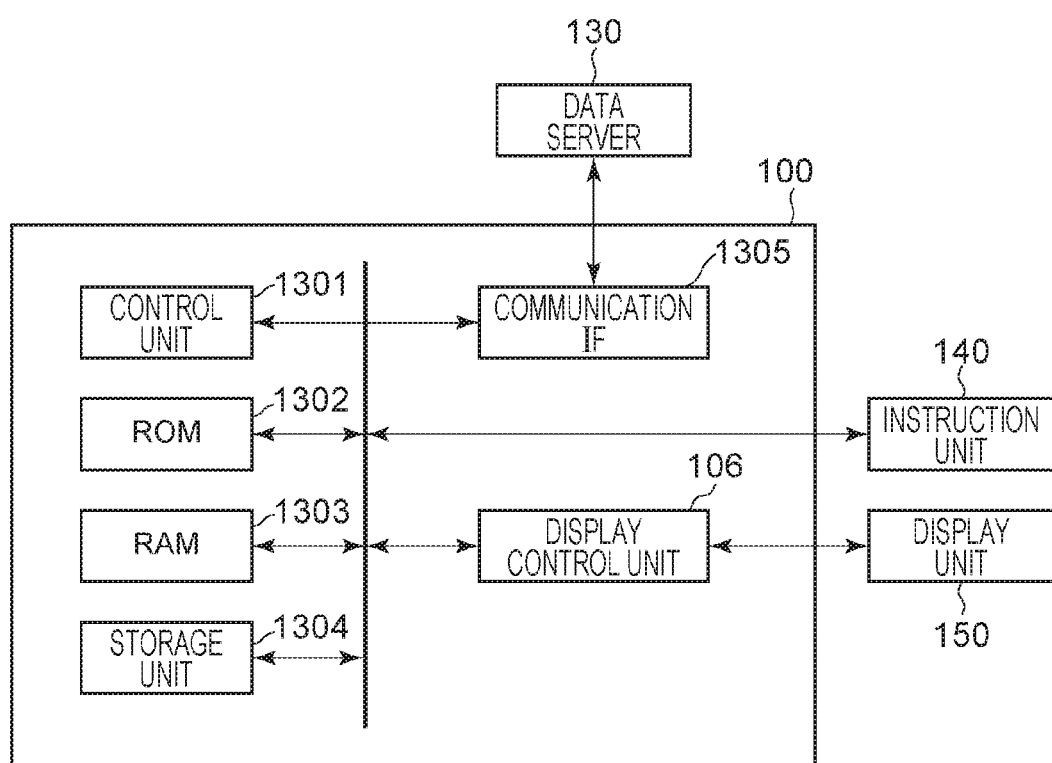
FIG. 13 is a diagram illustrating the hardware configuration of an information processing apparatus.

Referring to FIG. 1 and FIG. 13, description is given of the data server 130 that is separated from the information processing apparatus 100 as an example. However, a partial area in the storage unit 1304 may be reserved, and the area may be considered as the data server. In addition, referring to FIG. 1, description is given of the information processing apparatus 100 that is a single apparatus as an example. However, by using cloud computing, any hardware resource, such as the control unit 1301 or the storage unit 1304, may be used via the Internet.

Referring back to FIG. 1, the control unit 1301 of the information processing apparatus 100 includes constituent elements described below. An instruction acquisition unit 101 acquires a user instruction from the instruction unit 140. An image information acquisition unit 102 acquires medical image data input to the information processing apparatus 100. An image processing unit 103 performs image processing on a combination of a plurality of medical images acquired from the image information acquisition unit 102 and acquires the result of image processing. A history information management unit 104 stores history information including identification information of a combination of medical images that has already undergone image processing. In addition, upon receiving an inquiry from an already-processed state determination unit 105, the history information management unit 104 sends back the history information. The already-processed state determination unit 105 searches the history information on the basis of the identification information of the acquired medical image and determines whether a predetermined medical image has already been processed. The display control unit 106 performs control to output information, such as the acquired result of image processing, to the display unit 150. In addition, the display control unit 106 displays the information indicating the medical image determined to have been processed, distinctively from the medical images determined not to have been processed.

The display unit 150 may be any display device, such as an LCD or a CRT. The display unit 150 displays a medical image or the like for a medical doctor to perform interpretation of radiogram. More specifically, the display unit 150 provides a GUI for a user, such as medical doctor, to select, from an examination list for the patient, a first selection image and a second selection image that are to undergo image processing. If the target medical image is a three-dimensional image, the display unit 150 displays the cross-sectional images of the first selection image and the second selection image acquired from the information processing apparatus 100. In addition, the display unit 150 displays the images resulting from the image processing performed on these images. The display unit 150 further provides a GUI for acquiring an instruction from a user, such as a medical doctor. By using the above-described GUIs, the user can freely switch the cross-sectional image of the first selection image, the second selection image, and the resultant image of image processing that are being displayed to another cross-sectional image in the depth direction of the cross-sectional images.

In the information processing system according to the present embodiment, the information processing apparatus 100 and the data server 130 are installed at physically separated locations and are connected via a network. However, the device configuration is not necessarily limited thereto. For example, the information processing apparatus 100 and the data server 130 may be integrated into one body. In this case, the input/output of data via the network between the information processing apparatus 100 and the data server 130 can be replaced with the input/output of data in the same apparatus. More specifically, a process of transmitting a requested medical image from the data server 130 to the information processing apparatus 100 and a process of transmitting the result of image processing generated by the information processing apparatus 100 to the data server 130 are replaced with data input/output in the same apparatus. Alternatively, the constituent elements of the information processing apparatus 100 illustrated in FIG. 1 may be shared by a plurality of apparatuses. For example, an information processing apparatus A may include the constituent elements from the instruction acquisition unit 101 to the already-processed state determination unit 105, and an information processing apparatus B may include the display control unit 106. Then, the information processing apparatuses A and B may cooperate to provide a form that implements the present embodiment.

Figure 2:
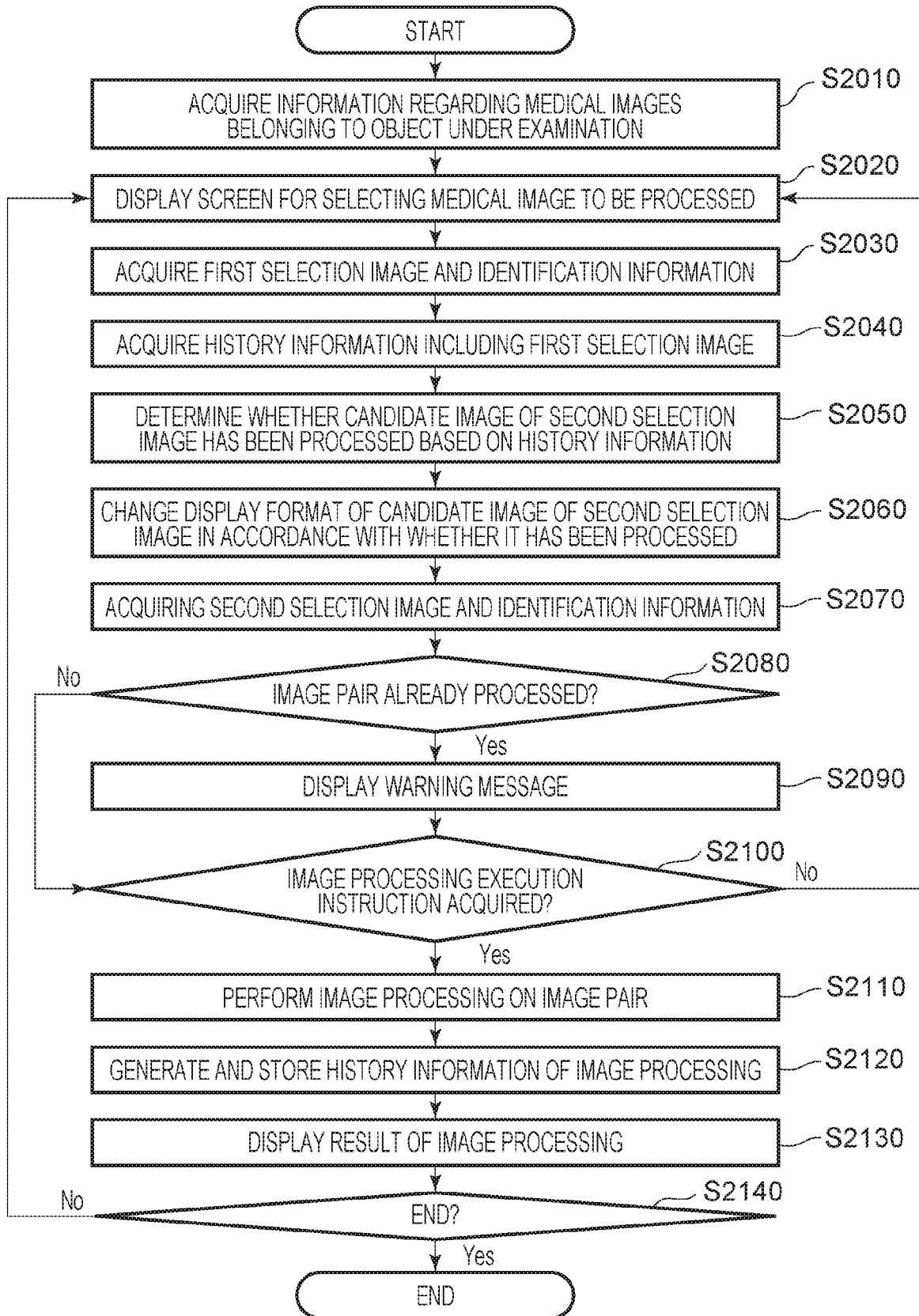
FIG. 2 is a flowchart illustrating the overall processing procedure according to the first embodiment.

FIG. 2 is a flowchart illustrating the overall processing procedure performed by the information processing apparatus 100.

(S2010) (Acquiring Information Regarding Medical Images Belonging to Object Under Examination)

In step S2010, the image information acquisition unit 102 acquires, via the instruction acquisition unit 101, the image information regarding the medical image belonging to a patient specified using the instruction unit 140. For example, the instruction acquisition unit 101 receives an instruction to select a specific patient selected by the user from a patient list (not illustrated) displayed on the display unit 150. The patient list has information about a plurality of patients listed therein. Furthermore, the image information acquisition unit 102 acquires, from the data server 130, the data of a plurality of medical images belonging to the patient ID of the selected patient. Note that the technique for acquiring the data of the medical images is not limited thereto, and another technique may be used. For example, the image information acquisition unit 102 may acquire, from the data server 130, the data of a plurality of medical images belonging to the patient ID set forth in the incidental information of the specific medical image selected by the user. Thereafter, the image information acquisition unit 102 outputs the data of the plurality of medical images to the display control unit 106.

(S2020) (Displaying Screen for Selecting Medical Image to be Processed)

In step S2020, the display control unit 106 causes the display unit 150 to display a selection screen for selecting a medical image that is to undergo image processing on the basis of the acquired data of the plurality of medical images. More specifically, the display control unit 106 generates thumbnail images from the image data of the plurality of medical images, classifies the thumbnail images for each of examination IDs (study IDs) stored in the incidental information of the medical images, and displays the list of thumbnail images.

Figure 3:
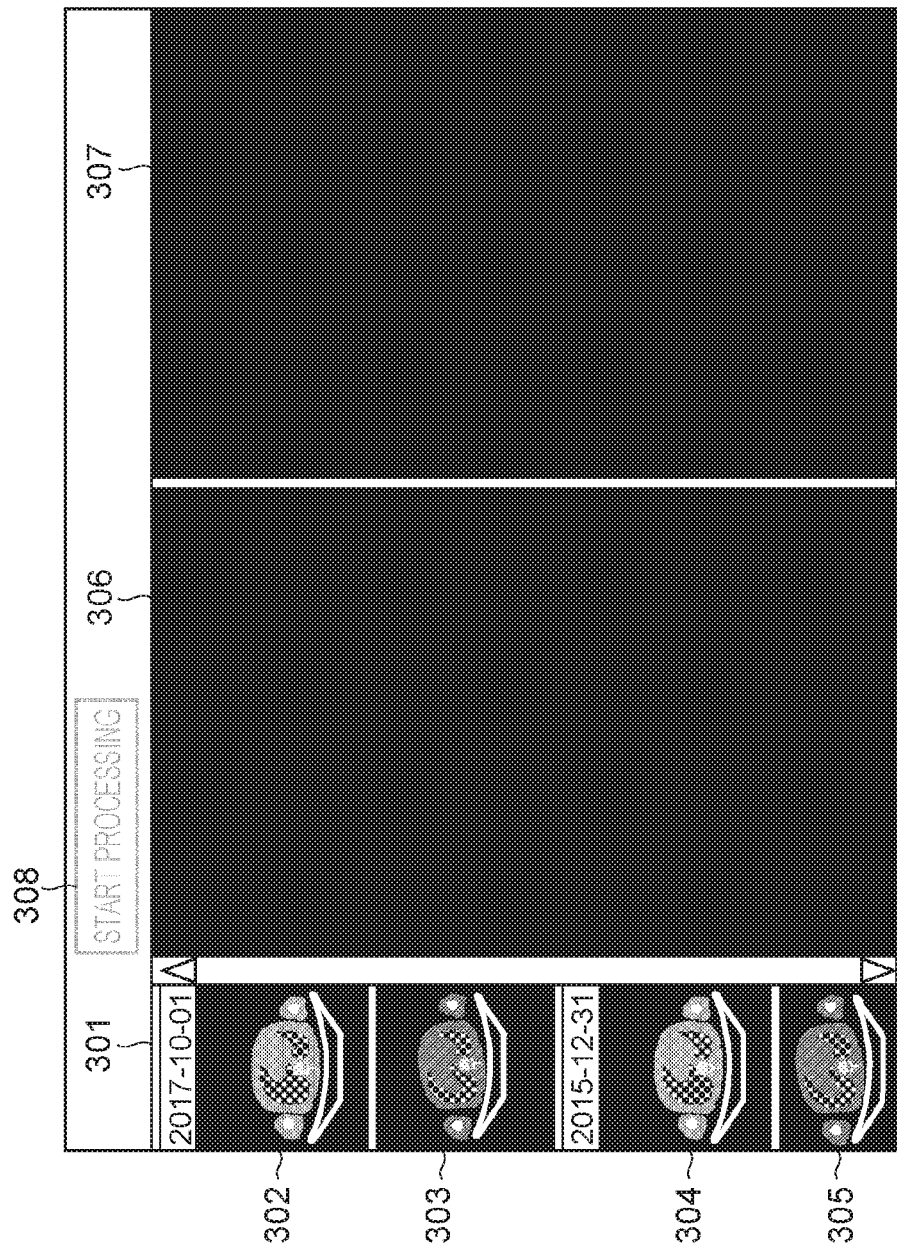
FIG. 3 is a diagram illustrating an example of a window for selecting a medical image to be processed.

FIG. 3 is a diagram illustrating an example of a screen for selecting a medical image to be processed. "301" represents an examination list in which medical images obtained through a plurality of examinations carried out in the past for a specific patient are listed and displayed. In the examination list 301, the thumbnail images corresponding to the individual medical images are classified by examination date (or study) and are displayed (e.g., "302" and "303" (examination date: 2017 Oct. 1) and "304" and "305" (examination date: 2015 Dec. 31)). Note that in this example, the medical images are CT image obtained by a CT scan. However, the medical images may be images captured by another modality. In addition, "306" and "307" represent display areas for observing the selected medical images in detail. In FIG. 3, since nothing is selected, nothing is displayed in the display areas. In this example, image processing is performed on a combination of two images and, thus, two display areas are provided. The user can select an image by, for example, dragging and dropping any one of the thumbnail images displayed in the examination list 301 to the display area 306 or 307. Note that the image selection technique is not limited thereto. For example, the image may be selected by right-clicking a thumbnail image to display a menu and selecting one of the areas in which the image is to be displayed. "308" represents a button used to start image processing, which is enabled only after the combinations of medical images to be processed are selected. In this example, the button 308 is disabled because the medical images have not been selected.

Note that according to the present embodiment, the thumbnail images of medical images are displayed on the selection screen in the form of a list as the examination list. However, the unit for allowing the user to select a medical image is not limited thereto. Any unit that displays the information representing each of the medical images separately to allow selection of the image can be employed. For example, a character string of identification information (a series ID) of each medical image may be displayed in the examination list, and the user may select the medical image by designating the character string.

(S2030) (Acquiring First Selection Image and Identification Information)

In step S2030, the image information acquisition unit 102 identifies the first selection image to be processed on the basis of an instruction acquired by the instruction acquisition unit 101 to select the first selection image. More specifically, in the case where the first selection image has not been selected in the examination list 301, the image information acquisition unit 102 waits until the instruction to select the first selection image is acquired. In contrast, in the case where the first selection image has already been selected, if a new selection instruction of the first selection image is acquired, the image information acquisition unit 102 identifies the newly selected medical image as the first selection image. However, if the selection instruction is not acquired, the image information acquisition unit 102 identifies the selected medical image as the first selection image.

Note that as in step S2050 (described below), if the type of image processing is such that two medical images that are to undergo image processing have different roles, such as an image having a first role and an image having a second role, the processing may be performed as follows. That is, in this step, the first selection image is acquired together with the role information of the first selection image. In this case, an example of the image processing in which the roles are different is a subtraction image generation process that generates a subtraction image between two images. That is, the image processing is image processing for calculating a difference between pluralities of medical images. In the subtraction image generation process, the images have different roles—one has a role of a first image (a standard image or a reference image) serving as the minuend (A in A–B) while the other has a role of a second image (a comparison image or a floating image) serving as the subtrahend (B in A–B). That is, the two images are a reference image functioning as a reference for image processing and a comparison image that is to be compared with the reference image. To acquire the role, the display area 306 in FIG. 3 is defined as an area for the user to specify a comparison image, for example. When a medical image is dragged and dropped into the display area 306, the image (the first selection image) is determined to be the comparison image. In addition, the display area 307 is defined as an area for the user to specify the reference image. When a medical image is dragged and dropped into the display area 307, the image (the first selection image) is determined to be the reference image. Note that if as described below, the roles of the images are determined in accordance with the relationship between the first selection image and the second selection image, the determination of the roles in this step is not needed. In addition, if the type of image processing is such that the roles of the two medical images that are to undergo image processing are not distinguished (for example, super-resolution image generation processing from two images), the determination of a role is not made.

Subsequently, the image information acquisition unit 102 outputs the image data of the identified first selection image to the image processing unit 103 and the display control unit 106. Furthermore, the image information acquisition unit 102 outputs the identification information of the selected first selection image to the already-processed state determination unit 105.

(S2040) (Acquiring History Information Including First Selection Image)

In step S2040, the already-processed state determination unit 105 inquires about the history information held by the history information management unit 104 on the basis of the acquired identification information of the first selection image and acquires the history information including the identification information of the first selection image. That is, the history information management unit 104 corresponds to an example of an acquisition unit configured to acquire the history information regarding image processing using a plurality of medical images. As used herein, the term "history information" refers to information having, recorded therein, combinations of already processed medical images including a combination of identification information of medical images that have already undergone image processing. In addition, the history information management unit 104 holds a history information list in which individual history information corresponding to a combination of processed medical images is listed.

FIG. 4 is a diagram illustrating an example of the information in the history information list. In the example illustrated in FIG. 4, the type of image processing indicates image processing in which the images have different roles (for example, subtraction image generation processing). The history information list stores history IDs each identifying individual history information. In addition, in the individual history information, each of the history IDs has, associated therewith, a series ID identifying an image having a first role (the "reference image" in FIG. 4) and a series ID identifying an image having a second role ("comparison image" in FIG. 4) that have already undergone image processing. Furthermore, the history ID has, associated therewith, a parameter ID that identifies the image processing parameter at this time and a series ID that identifies the resultant image obtained through the image processing.

As a specific process of this step, the already-processed state determination unit 105 searches the history information list by using the identification information of the first selection image acquired in step S2030 as a key. The processing is described below with reference to an example in which the identification information (the series ID) of the first selection image in FIG. 4 is "0000010". At this time, if the first selection image is the image having the first role (that is, if the first selection image is selected as the reference image), the already-processed state determination unit 105 extracts a history information item including identification information of the first selection image as the image having the first role. In the example illustrated in FIG. 4, the history ID "002" including the series ID "0000010" in "reference image" is extracted. Thereafter, the already-processed state determination unit 105 acquires the following information associated with the history ID:

the series ID of the comparison image: "0000020"
the parameter ID: "01"
the series ID of the processing result image: "1000002"

In contrast, if the first selection image is the image having the second role (that is, if the first selection image is selected as the comparison image), the already-processed state determination unit 105 extracts the history information item including identification information of the first selection image as the image having the second role. In the example illustrated in FIG. 4, the history ID "005" including the series ID "0000010" in "comparison image" is extracted. Thereafter, the already-processed state determination unit 105 acquires the following information associated with the history ID:

the series ID of the reference image: "0012345"
the parameter ID: "02"
the series ID of the processing result image: "1000005"

However, if the role of the first selection image is not determined, the already-processed state determination unit 105 extracts the history ID including the series ID "0000010" in either "reference image" or "comparison image" (in the example illustrated in FIG. 4, the history IDs "002" and "005" are extracted).

Note that if the type of image processing indicates image processing in which the roles of the two medical images are not distinguished, the history information is also stored without distinguishing the roles of the images. In this case, the two images are saved as "medical image 1" and "medical image 2". In this case, all the histories each including the identification information of the first selection image in either "medical image 1" or "medical image 2" are extracted.

In this manner, as the history information item including the identification information of the first selection image, it is possible to acquire the medical image that has undergone the image processing in combination with the first selection image, the processing parameter, and the information about the processing result image. Note that the history information item is not limited to the information illustrated in FIG. 4. The history information item may be any information that includes a combination of identification information of already processed medical images. For example, the processing parameter and the identification information of the processing result image may not necessarily be included.

(S2050) (Determining Whether Candidate Image of Second Selection Image has Already been Processed Based on History Information)

In step S2050, the already-processed state determination unit 105 determines whether each of candidate images of the second selection image selected next to the first selection image has already been processed in combination with the first selection image on the basis of the history information item extracted in step S2040. That is, the already-processed state determination unit 105 corresponds to an example of a determination unit configured to determine, by using the acquired history information item, whether each of candidate images of the second medical image used in the image processing together with the first medical image selected by the operator has already undergone the image processing performed together with the first medical image. More specifically, the already-processed state determination unit 105 acquires, as the information about the candidate images of the second selection image, the identification information indicating each of the medical images other than the first selection image among the medical images acquired in step S2010. Thereafter, for each of the candidate images of the second selection image, the already-processed state determination unit 105 determines whether the identification information of the image is included in the history information item extracted in step S2040.

At this time, in the case where the first selection image is determined to be the image having the first role (for example, the reference image), if the history information item holding the identification information of the candidate image as the image having the second role (for example, the comparison image), the already-processed state determination unit 105 determines that the candidate image has already been processed. However, in the case where the first selection image is determined to be the image having the second role (for example, the comparison image), if the history information item holding the identification information of the candidate image as the image having the first role (for example, the reference image) is extracted, the already-processed state determination unit 105 determines that the candidate image has already been processed. As described above, in the case where the roles of the medical images that are to undergo image processing are different, only when the combination of medical images is set forth in the history information item and the role of the medical image set forth in the history information item is the same as the identification information, it is determined that the combination of medical images has already been processed. As a result, the risk of wrong determination that a combination has already been processed is eliminated when selection is made so that the combination of images that are to undergo image processing matches the history information item but the role is different from in the history information.

For example, suppose that in FIG. 4, the image of the identification information "0000010" is specified as the reference image and is selected as the first selection image, and the history information item of the history ID "002" is extracted through the process in step S2040. At this time, in the example illustrated in FIG. 4, if the series ID of the candidate image of the second selection image is "0000001", the series ID is not included in the history information item extracted in step S2040. Therefore, the already-processed state determination unit 105 determines that "processed: False" is set. However, if the series ID of the candidate image of the second selection image is "000020", the extracted history information item (the history ID "002") includes the series ID indicating a comparison image ("medical image 2"). Therefore, the already-processed state determination unit 105 determines that "processed: True" is set.

In addition, if the role of the first selection image is not determined, the already-processed state determination unit 105 determines the role of each of the images in accordance with the relationship between the first selection image and each of the candidate images. Thereafter, when the history information item holding the identification information of the candidate image is extracted as the image of the determined role, the already-processed state determination unit 105 determines that the candidate image has already been processed. For example, the role can be determined on the basis of the incidental information of the first selection image and the candidate image. As a more specific example, the roles can be determined such that one image with a more recent capture date is a reference image, and the other is a comparison image. For example, in the example illustrated in FIG. 4, suppose that the image of the identification information "0000010" is selected as the first selection image without a role specified, and the history information items of the history IDs "002" and "005" are extracted through the process in step S2040. Note that for convenience of description, the capture date of the image "0012345" is more recent than that of the image "0000010", which is more recent than that of the images "0000020". At this time, if the identification information of the candidate image is "0000020", the already-processed state determination unit 105 compares the image capture date of the first selection image with the image capture date of the candidate image. Then, the already-processed state determination unit 105 determines the image with a more recent capture date (image "0000010") to be the reference image and determines the image with the less recent capture date (image "0000020") to be the comparison image. As a result, the combination of the images having these roles matches the history ID "002". Accordingly, the already-processed state determination unit 105 determines that the combination corresponds to "processed: True". However, if the identification information of the candidate image is "0012345", the already-processed state determination unit 105 determines that the image with a more recent date (image "0012345") to be the reference image and determines the image with the less recent date (image "0000010") to be the comparison image. As a result, the combination of the images having these roles matches the history ID "005". Accordingly, the already-processed state determination unit 105 determines that the combination corresponds to "processed: True".

Furthermore, if the type of image processing indicates image processing in which the roles of two medical images that are to undergo image processing are not distinguished, the determination is made as follows. That is, if in the extracted history information, the identification information of the candidate image is included in either "medical image 1" or "medical image 2", the already-processed state determination unit 105 determines that the combination corresponds to "processed: True".

As described above, by determining whether the identification information of each of the candidate images of the second selection image is included in the history information item including the identification information of the first selection image, it can be determined whether the candidate image has already been processed in combination with the first selection image.

However, the criterion for determining whether a combination has already been processed is not limited thereto. For example, only if an image has undergone image processing in combination with the first selection image by using the same parameter as the parameter (the setting information) of the currently set image processing (the image processing performed by the image processing unit 103 in step S2110), it may be determined that the combination has already been processed. That is, only if the identification information of the candidate image of the second selection image is set forth and a parameter ID that is the same as the processing parameter of the currently set image processing is set forth in the same history information item, it is determined that the combination has already been processed. In this manner, for example, even if a candidate image is the medical image that has undergone image processing in combination with the first selection image in the past, the candidate image can be determined not to have been processed if the processing parameter differs from the currently set processing parameter. Accordingly, the user can perform image processing on even the same medical image combination by changing the processing parameter.

Subsequently, the already-processed state determination unit 105 transmits, to the display control unit 106, determination information as to whether each of the candidate images of the second selection image has already been processed.

(S2060) (Changing Display Format of Candidate Image of Second Selection Image in Accordance with Whether Candidate Image has been Processed)

In step S2060, the display control unit 106 changes the display format of each of the candidate images of the second selection image in the examination list on the basis of the determination information as to whether the candidate image of the second selection image has already been processed. That is, the display control unit 106 corresponds to an example of an output unit configured to output a notification in accordance with the result of the determination.

Figure 5:
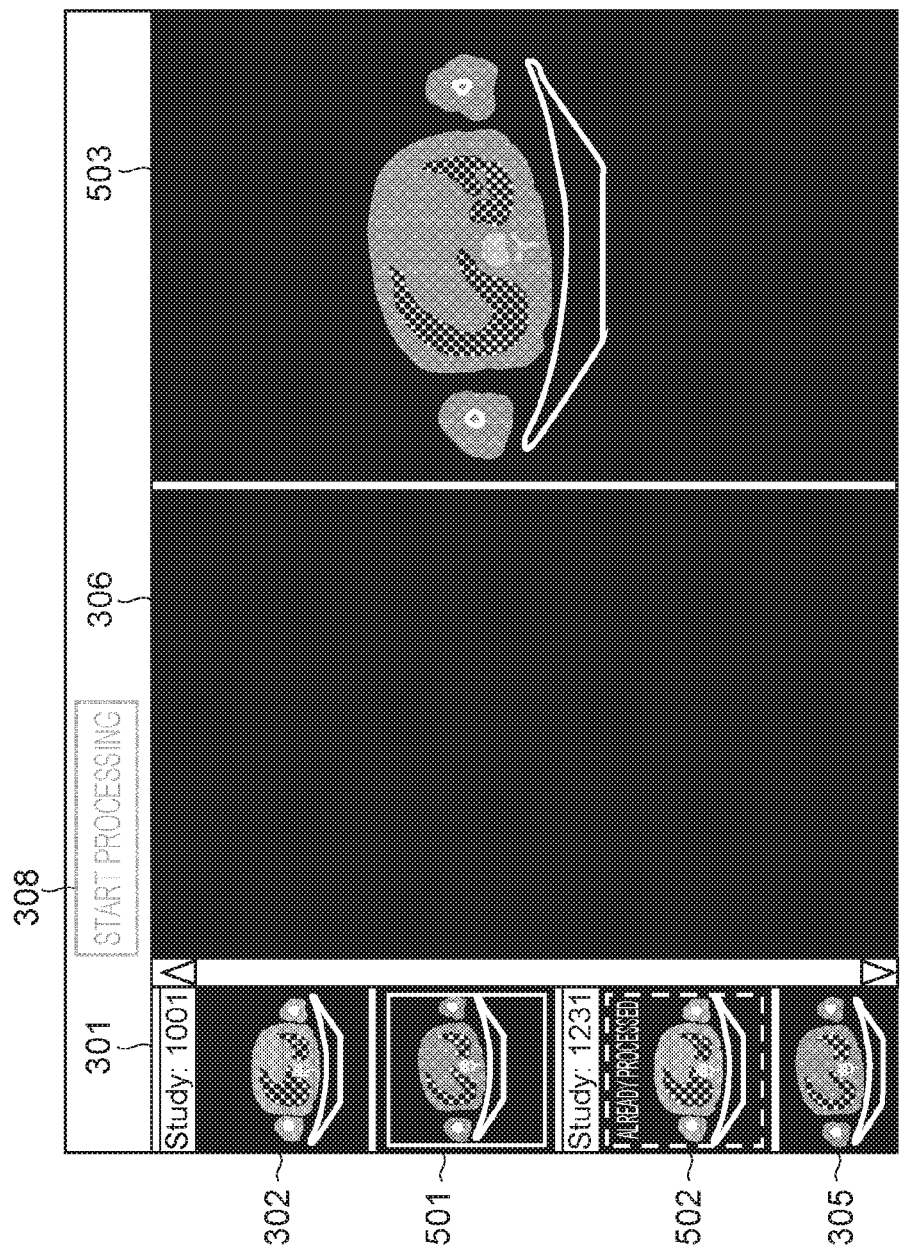
FIG. 5 is a diagram illustrating the processed images that are distinctively displayed at the time of selection of the first selection image.

FIG. 5 is a diagram illustrating the processed images distinctively displayed at the time of selection of the first selection image. "501" represents a thumbnail image (corresponding to the thumbnail image 303 before the selection is made) of the first selection image selected by the user. "503" represents a cross-sectional image of the first selection image displayed when the user selects the first selection image. Furthermore, "502" represents a thumbnail image (the information regarding a candidate image) of a candidate image of the second selection image determined to have been processed ("processed: True"). In this GUI, a rectangular frame denoted by a dotted line is displayed together with the character string "processed". In addition, "302" and "305" represent the thumbnail images of the candidate images of the second selection image determined not to have been processed ("processed: False"), which have the same image format as that of the images denoted by "302" and "305" in FIG. 3. As described above, the display format of the thumbnail image is changed in accordance with whether the medical image has already been processed. In addition, the medical image that has already been processed is displayed such that the user can get to know the processed image has already been processed. In this way, the user can easily check which medical image has been processed in combination with the first selection image 501.

Note that the method for changing the display technique of a candidate image of the second selection image in accordance with whether the candidate image has already been processed is not limited thereto. Any method by which a user can identify a candidate image of the processed second selection image can be employed. For example, the character string "processed" need not be displayed, or the rectangular frame with a dotted line need not be displayed. The character string "unprocessed" may be displayed on the thumbnail image of a candidate image of the second selection image that is determined not to have been processed. Alternatively, the color of the thumbnail image may be changed in accordance with whether the thumbnail image has been processed. Still alternatively, only when the user puts a cursor on the thumbnail image of the candidate image of the second selection image that is determined to have been processed, the display format may be changed from that of the candidate image of the second selection image that is determined not to be have been processed. Yet still alternatively, the audio data indicating that the image processing using the image denoted by "501" and the image denoted by "502" has already been processed may be played back and may be output from a loudspeaker (not illustrated).

Note that if the reference image is selected as the first selection image, the process of changing the display format of the candidate images that have been processed may be performed, while if the comparison image is selected as the first selection image, the following operation may be selected. That is, the display format of the candidate image that is a member of the processed combination is not changed.

Through the above-described processing, in response to selection of the first selection image by the user, processing is performed for changing the display format of the candidate image of the second selection image in the display area for allowing the user to select the second selection image. Note that if the user reselects (changes) the first selection image, the above-described processing is performed again on the newly selected first selection image. Note that if the first selection image is selected again, the first selection image may be deselected, and the display format of the processed candidate image of the second selection image may be changed back to the original format. That is, the output of the notification is stopped.

(S2070) (Acquiring Second Selection Image and Identification Information)

In step S2070, the image information acquisition unit 102 identifies the second selection image to be processed in combination with the first selection image on the basis of the selection instruction of the second selection image acquired by the instruction acquisition unit 101. The basic process is obtained only by replacing the first selection image in step S2030 with the second selection image and, thus, description of the process is not repeated. Note that even when the second selection image is selected, the display format of the candidate image of the processed second selection image displayed in step S2060 remains unchanged. However, the display method is not limited thereto. At the same time that the second selection image is selected, the display format of the processed candidate images may be changed to a display format similar to that of other unprocessed candidate images.

Thereafter, the image information acquisition unit 102 outputs the image data of the identified second selection image to the image processing unit 103 and the display control unit 106. Furthermore, the image information acquisition unit 102 outputs the identification information of the selected second selection image to the already-processed state determination unit 105.

(S2080) (has Image Pair Already been Processed?)

In step S2080, the display control unit 106 moves the process to step S2090 if the acquired image pair consisting of the first selection image and the second selection image has already been processed. However, if the acquired image pair has not been processed, the display control unit 106 moves the process to step S2100. That is, if the identification information of the candidate image determined to have already been processed in S2050 is acquired as the second selection image, the determination is "Yes". However, if the identification information of the candidate image determined not to have been processed is acquired, the determination is "No".

(S2090) (Displaying Warning Message)

In step S2090, the display control unit 106 displays a warning message indicating that the pair consisting of the selected first selection image and second selection image has already been processed.

Figure 6:
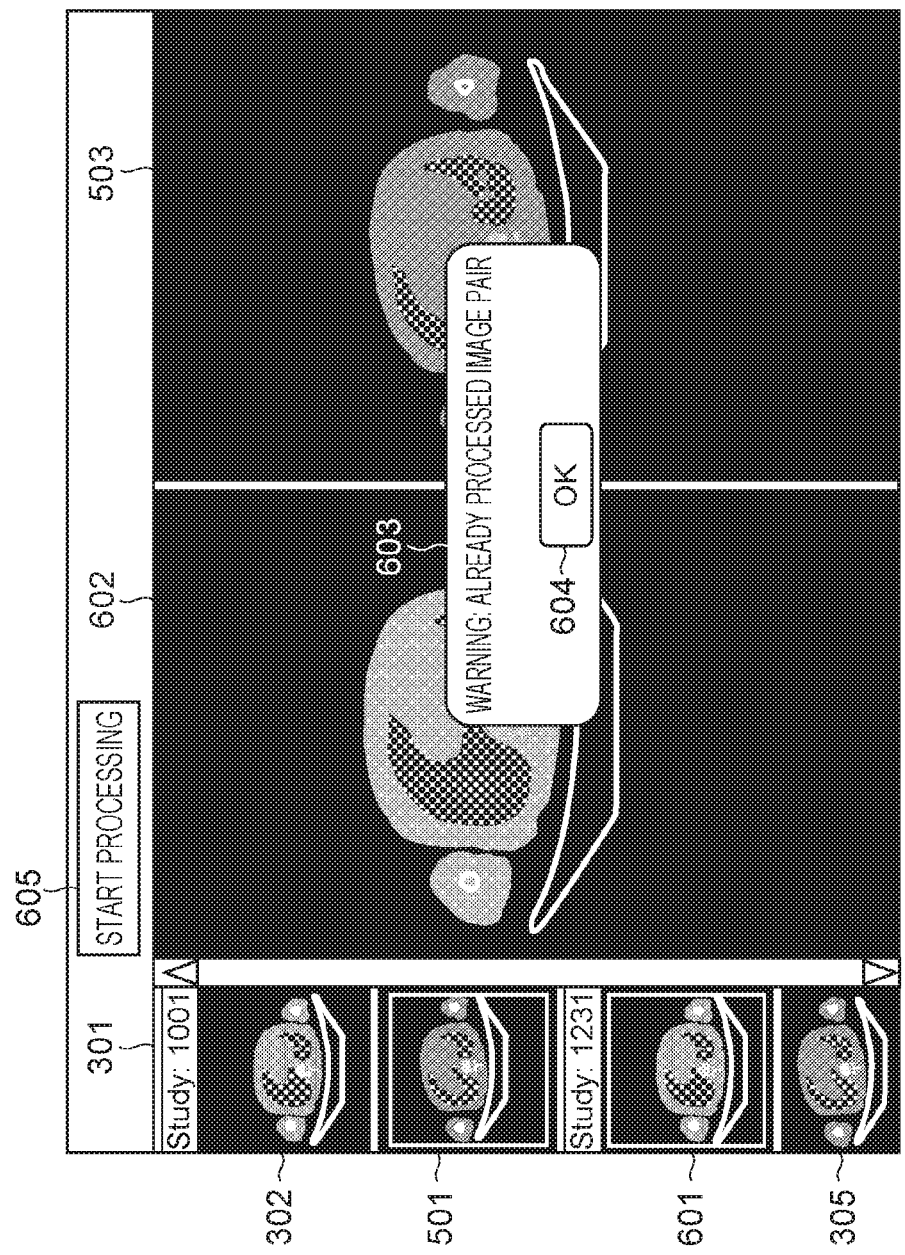
FIG. 6 is a diagram illustrating a window in which a warning message is displayed when a processed image pair is selected.

FIG. 6 is a diagram illustrating a window in which a warning message is displayed when a processed image pair is selected. "601" represents the thumbnail image of a second selection image selected by the user even though information indicating that the second selection image has already been processed is displayed in the thumbnail image 502 in FIG. 5. In addition, "602" represents a cross-sectional image of the second selection image displayed when the user selects the thumbnail image 601 of the second selection image. "603" represents a displayed warning pop-up window indicating that the pair consisting of the selected first selection image 501 and second selection image 601 has already been processed. By displaying the pop-up window 603, the user can easily get to know that the selected image pair has already been processed. "604" represents an OK button used to close the pop-up window. Note that the warning display method is not limited thereto. For example, a character string indicating a warning may be directly displayed on the cross-sectional images 602 and 503 in a superimposed manner or may be displayed in a predetermined display area. In addition, "605" represents a button used to start image processing that is enabled by selecting a combination of medical images to be processed.

Subsequently, if an instruction indicating the approval of the user (pressing the OK button 604 by the user) is acquired, the processing proceeds to step S2100.

(S2100) (Is Image Processing Execution Instruction Acquired?)

In step S2100, the instruction acquisition unit 101 moves the process to step S2120 if the user's instruction to perform the image processing is acquired. However, the instruction acquisition unit 101 moves the process to step S2020 if the instruction is not acquired. The instruction to perform the image processing can be acquired from the user when, for example, the user presses the button 605 in FIG. 6. Note that the method for acquiring the instruction to perform image processing is not limited thereto. For example, a method may be used in which a pop-up window is displayed that acquires an execution instruction at the same time when two image pairs are selected, and the user presses the OK button displayed on the pop-up window.

(S2110) (Performing Image Processing on Image Pair)

In step S2110, the image processing unit 103 uses, as an input, the image data of the first selection image and the second selection image acquired from the image information acquisition unit 102 and performs image processing. At this time, if roles are set for the selected images, the image processing unit 103 performs image processing based on the roles. More specifically, according to the present embodiment, the image processing is performed by performing a registration process such that the anatomical structure extracted from the first selection image matches that extracted from the second selection image (the comparison image is registered to the reference image) and, thereafter, performing a subtraction image generation process for generating a subtraction image between the two images after the registration process is completed. In this example, the registration technique may be any widely used technique. Note that the image processing performed on the combination of the first selection image and the second selection image is not limited thereto. Any image processing that is performed on a combination of two images may be employed. For example, only the registration process between two medical images may be performed. In this case, the registration process between the first selection image and the second selection image produces registered images in which either one is registered to the other.

Subsequently, the image information acquisition unit 102 stores the generated image processing result in a database (not illustrated) and outputs, to the history information management unit 104, the identification information of the first selection image and the second selection image and the identification information of the generated image which is the image processing result.

(S2120) (Generating and Storing History Information Regarding Image Processing)

In step S2120, the history information management unit 104 newly generates history information that associates the acquired identification information of the first selection image and the acquired second selection image with the identification information of the resultant image of the image processing. For example, suppose that the history information list in FIG. 4 is already managed. In addition, the identification information (the series IDs) of the first selection image and second selection image that newly underwent image processing and the resultant image of the image processing are "0000010", "0000030", and "1000006", respectively. At this time, the history ID "006" is newly issued, and these pieces of identification information are associated with the history ID and are stored. At this time, if roles are set for the selected images, the pieces of identification information are saved in a format that distinguishes the roles. Note that if the processing parameter used when the image processing is performed is "01", the parameter ID of the processing parameter is also associated with the history ID and is stored. Similarly to step S2040, the history information item does not necessarily have to store the processing parameter and the identification information of the processing result image.

(S2130) (Displaying Result of Image Processing)

In step S2130, the display control unit 106 causes the display unit 150 to display the resultant image of the image processing acquired from the image information acquisition unit 102. More specifically, the display control unit 106 displays the cross-sectional images of the first and second selection images and the cross-sectional image of the resultant image of the image processing. In this manner, the user can observe the first and second selection images while referring to the result of the image processing. If the result of image processing already exists, the resultant image of the image processing acquired from the database (not illustrated) can be displayed on the display unit 150.

(S2140) (End?)

In step S2140, the display control unit 106 ends the process if an end instruction is acquired from the user via the instruction unit 140. However, if the display control unit 106 does not acquire the end instruction, the display control unit 106 moves the process to step S2020, where the user is allowed to reselect a medical image to be processed.

As described above, the processing is performed by the information processing apparatus 100. Accordingly, if the user selects a first selection image from the displayed examination list, a candidate image of the second selection image that has already been processed in combination with the first selection image is displayed so that the user can recognize it from the examination list. Subsequently, if the user selects an unprocessed candidate image as the second selection image and instructs the execution of image processing, the image processing can be normally performed and the resultant image of the image processing cam be displayed. However, if the user selects a processed candidate image as the second selection image, a warning message is displayed that indicates that the selected image pair has already been processed. At this time, if the user who has received the warning message does not instruct execution of image processing, the selection screen of a medical image to be processed is displayed, and the user can reselect the medical image to be processed. However, if the user still instructs to perform the image processing even after receiving the warning message, the image processing can be performed as instructed, and the resultant image of the image processing can be displayed on the display unit 150.

According to the present embodiment, if the user specifies one of the medical images that has already undergone image processing, information about the medical image processed in combination with the specified image can be displayed so as to be distinguished from an unprocessed medical image. As a result, the probability of regenerating an image processing result that has already been generated by the user can be reduced, resulting in elimination of waste.

Modification 1-1

According to the first embodiment, the candidate image of the second selection image that has already been processed in combination with the first selection image in step S2060 is displayed distinctively from an unprocessed candidate image. In addition, if the image pair has already been processed, a warning message is displayed in step S2090. However, the technique for notifying the user that the image has already been processed need not be a two-step operation technique described above, and either one of the steps may be used. That is, only the display format of the candidate image of the second selection image that has been processed may be displayed distinctively from the others in step S2060, and the warning message display process in step S2090 need not be performed. Alternatively, the candidate image of the second selection image that has been processed may be displayed without distinction from the others in step S2060, and only the warning message display process in step S2090 may be performed. In this way, by notifying the user that the image has already been processed only once, a user can comfortably select an image to be processed without two-step messages that might be intrusive in some cases.

Modification 1-2

According to the first embodiment, the image processing is performed on a combination of two medical images. Thus, when the first selection image is selected, the candidate image of the second selection image is displayed distinctively from the others. However, the number of combinations of medical images that are to undergo image processing may be three or more. For example, when performing image processing on a combination of three medical images, the user selects medical images in the order of a first selection image, a second selection image, and a third selected image in a case list. At this time, as in the first embodiment, when the user selects the first selection image, the display control unit 106 displays a candidate image of the second selection image that has already been processed in combination with the first selection image, distinctively from the others. Subsequently, when the user selects the second selection image, the display control unit 106 displays a candidate image of the third selection image that has already been processed in combination with the first and second selection images, distinctively from the others. In this manner, even when image processing is performed on a combination of three medical images, the user can easily get to know an already processed medical image. At this time, in addition to the identification information of the two medical images, the identification information of the other medical image is stored in the history information list managed by the history information management unit 104. Thereafter, the history information items each including the identification information of the selected two images is searched for. Furthermore, among the retrieved history information items, it is determined that the third medical image set forth in the history information item including the identification information of both the selected images has already been processed, and the medical image can be displayed distinctively from the other medical images. Note that in this example, it is determined that the third medical image has already been processed if both the selected medical images are set forth in the history information item. However, it may be determined that the third medical image has already been processed if one of the selected two medical images is set forth in the history information item. In this case, a candidate image of the third selected image that has already been processed in combination with one of the first and second selection images can be displayed distinctively from the others.

Second Embodiment

According to the first embodiment, the information indicating the medical image that has already been processed in combination with the first selection image is displayed distinctively from the other medical images. In contrast, according to the present embodiment, selection of a medical image that has already been processed in combination with the first selection image as the second selection image is disabled. As a result, the probability can be further reduced of regenerating the image already generated as the result of image processing by the user. Thus, waste can be eliminated. The processing according to the present embodiment is described below with reference to FIGS. 7 to 8. Note that the configuration of an information processing system according to the present embodiment is the same as that in FIG. 1 and, therefore, description of the information processing system is not repeated.

Figure 7:
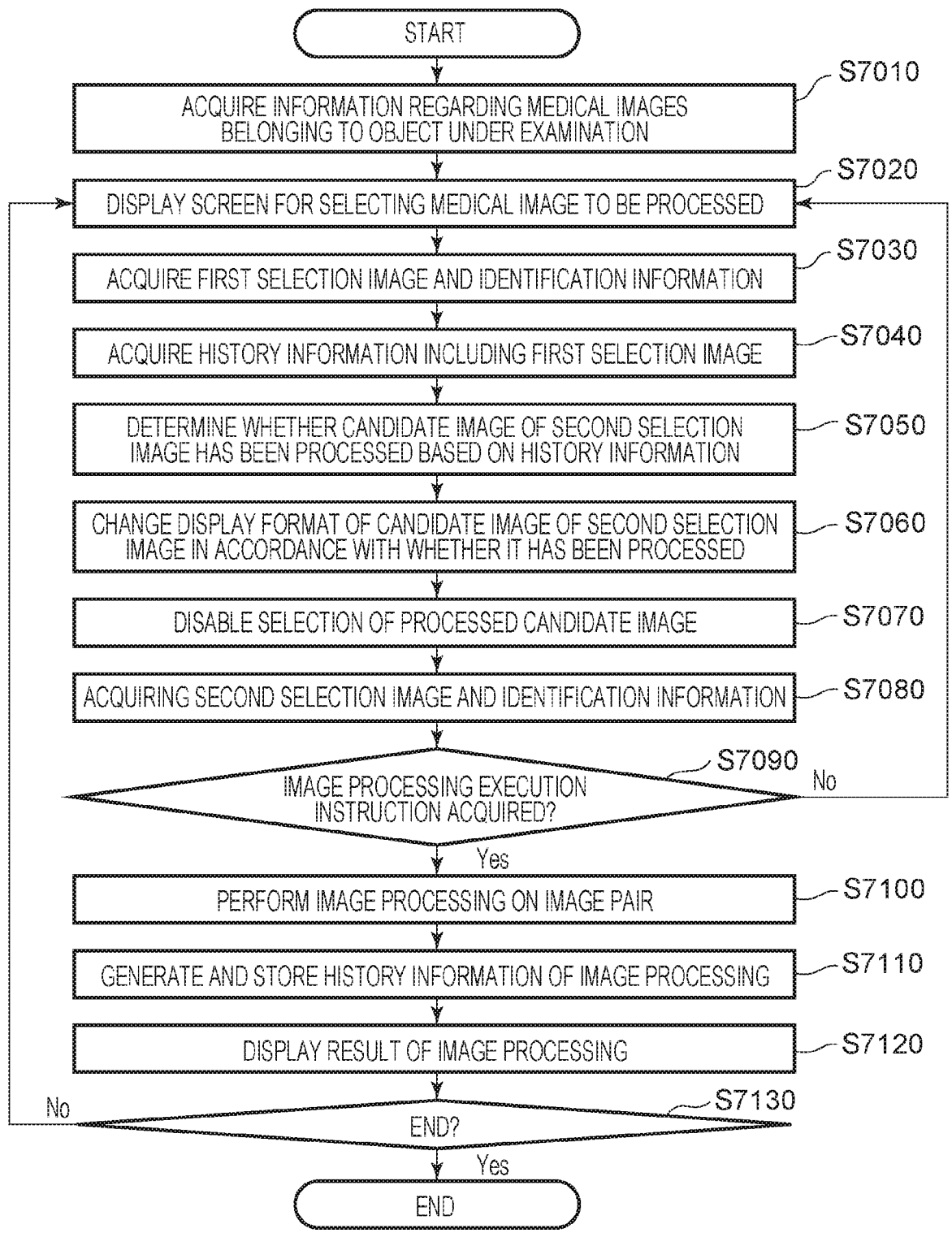
FIG. 7 is a flowchart illustrating the overall processing procedure according to a second embodiment.

FIG. 7 is a flowchart illustrating the overall processing procedure performed by an information processing apparatus 100. Note that in FIG. 7, the processes in steps S7010 to S7050, S7080, and S7090 to S7130 are the same as those of steps S2010 to S2050, S2070, and S2100 to S2140 in the flowchart illustrated in FIG. 2, respectively, and description of the processes are not repeated. Only the differences from the flowchart illustrated in FIG. 2 are described below.

(S7060) (Changing Display Format of Candidate Image of Second Selection Image in Accordance with Whether Candidate Image has been Processed)

In step S7060, as in step S2060, the display control unit 106 changes the display format of each of candidate images of the second selection image in the examination list on the basis of determination information as to whether the candidate image of the second selection image has already been processed. However, only the information displayed when the candidate image of the second selection image has already been processed is different from in step S2060 and, therefore, description other than a description of the different displayed information is not repeated.

Figure 8:
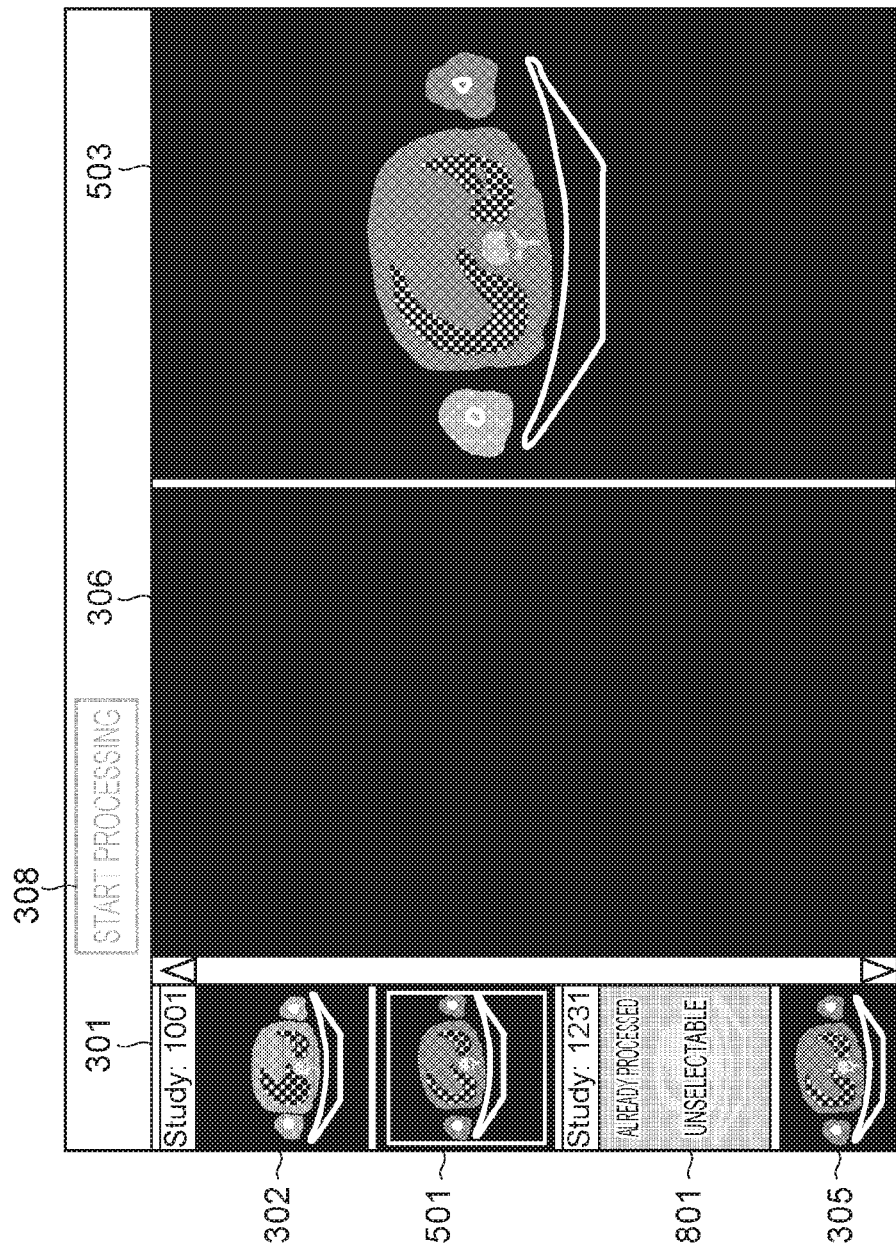
FIG. 8 is a diagram illustrating control performed so that an already processed image cannot be selected when the first selection image is selected.

FIG. 8 is a diagram illustrating control performed so that an already processed image cannot be selected when the first selection image is selected. "801" represents the thumbnail image of a candidate image of the second selection image determined to have already been processed. Like "502" illustrated in FIG. 5, the character string "unselectable" is displayed on the thumbnail image in addition to the character string "processed". In addition, the entire thumbnail image 801 is displayed in grayed-out color. In this way, by displaying the processed medical image such that the user can get to know that a processed medical image has already been processed and cannot be selected, the user can easily understand that the processed medical image cannot be selected.

It should be noted that the technique of changing the display method of a candidate image of the second selection image in accordance with whether the candidate image has been processed is not limited thereto. Any technique can be employed that causes the user to get to know that they cannot select a candidate image of the second selection image that has already been processed. For example, the thumbnail image may be grayed out without displaying the character strings "processed" and "unselectable". Conversely, the character strings "processed" and "unselectable" may be displayed without graying out the thumbnail image. Alternatively, if the candidate image has already been processed, the thumbnail image may be highlighted instead of being grayed out.

(S7070) (Making Processed Candidate Image Unselectable)

In step S7070, the display control unit 106 restricts selection of a candidate image of the second selection image that is determined to have already been processed in combination with the first selection image in step S7050. That is, this is an example of a restriction configured to restrict selection of a second medical image from among one or more candidate images determined to have already undergone image processing in combination with the first medical image. More specifically, if a cursor is put on the thumbnail image ("801" in FIG. 8) of the candidate image of the second selection image determined to have already been processed, the display control unit 106 disables the action of selecting the image (e.g., clicking or drugging the image). In this manner, the probability of an already processed image being selected by the user can be reduced. Note that the technique for disabling the selection of the candidate image determined to have already been processed is not limited thereto. For example, the information about the candidate image of the second selection image that is determined to have already been processed may be excluded from the displayed examination list so that the candidate image cannot be selected.

As described above, the processing is performed by the information processing apparatus 100. Thus, when the user selects a first selection image from the displayed examination list, information is displayed such that a candidate image of a second selection image that has already been processed in combination with the image of the first selection cannot be selected from the examination list. Subsequently, if the user selects an unprocessed candidate image as the second selection image, the user can instruct execution of the image processing to execute the image processing as usual and display the resultant image of the image processing. However, if the user attempts to select an already processed candidate image as the second selection image, the image selection action on the thumbnail image is disabled so that the processed image pair cannot be selected.

According to the present embodiment, if the user specifies, as the first selection image, one of the medical images that have already undergone image processing, the medical image that has already been processed in combination with the first selection image is not allowed to be selected as the second selection image. As a result, the probability can be reduced of regenerating the image already generated as the result of image processing by the user. Thus, waste can be eliminated.

Third Embodiment

According to the first embodiment, when the user specifies a pair of medical images that has already been processed through image processing, a warning message is only displayed. In contrast, according to the present embodiment, a warning message is displayed, and a selection instruction for displaying the image processing result can be acquired. If displaying the image processing result is selected, the image processing result is displayed. In this manner, when selecting a processed image pair, the user can easily get to know that the image pair has already been processed and easily examine the image processing result, which improves the efficiency of examining the image processing result. The processing according to the present embodiment is described below with reference to FIGS. 9 to 10. Note that the configuration of the information processing system according to the present embodiment is the same as that in FIG. 1 and, thus, description of the configuration is not repeated.

Figure 9:
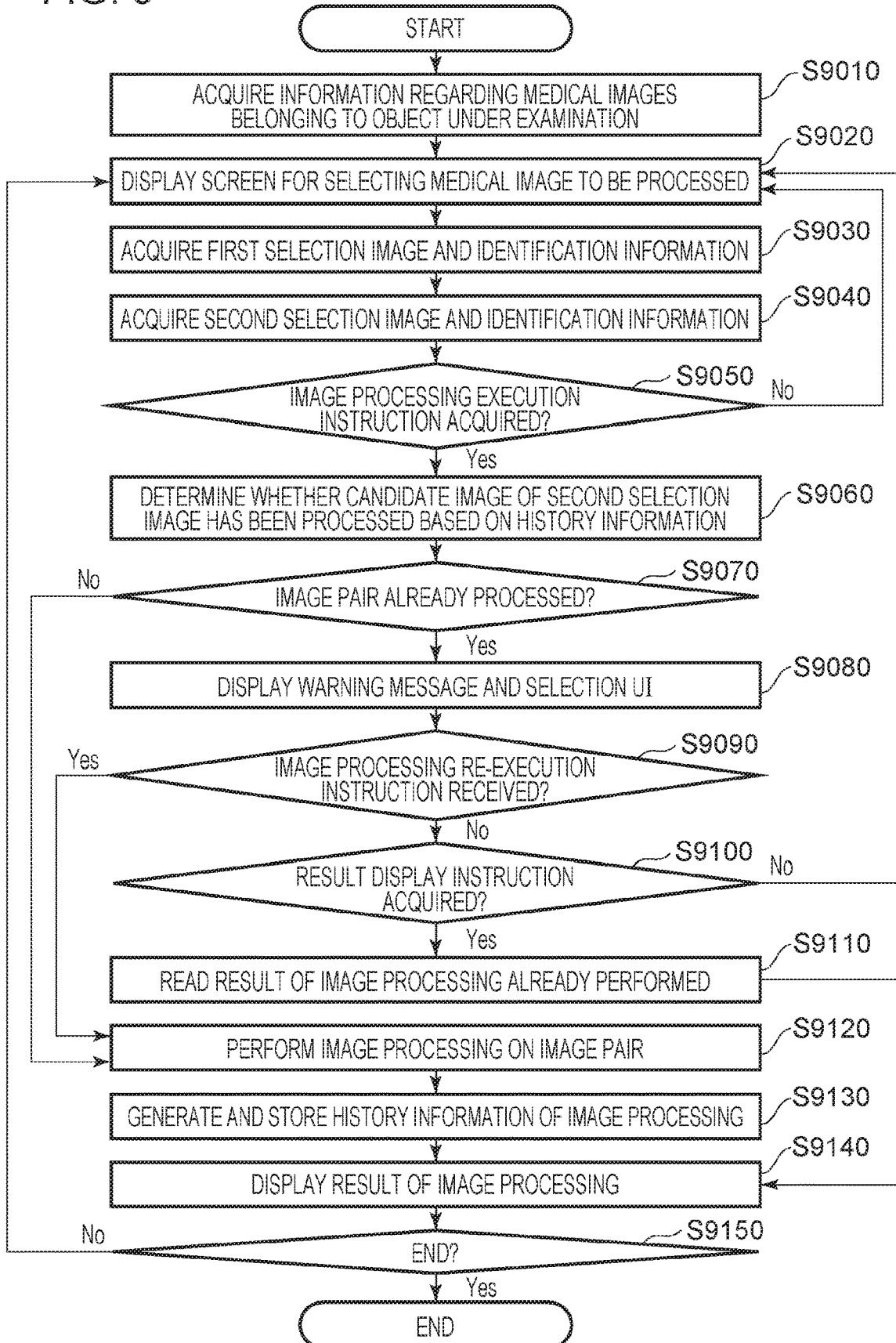
FIG. 9 is a flowchart illustrating the overall processing procedure according to the third embodiment.

FIG. 9 is a flowchart illustrating the overall processing procedure performed by the information processing apparatus 100. Note that in FIG. 9, the processes in steps S9010 to S9030, S9040, S9050, S9070, and S9120 to S9150 are the same as the following processes, respectively. That is, the processes are the same as the processes in steps S2010 to S2030, S2070, S2100, S2080, and S2110 to S2140 in the flowchart illustrated in FIG. 2. Therefore, description of the processes is not repeated. Only the differences from the flowchart illustrated in FIG. 2 are described below.

(S9060) (Determining Whether Image Pair has been Processed Based on History Information)

In step S9060, the already-processed state determination unit 105 determines whether the first and second selection images acquired in steps S9030 and S9040 have already been processed on the basis of the history information. More specifically, the already-processed state determination unit 105 searches the history information list held by the history information management unit 104 by using the combination of the identification information of the first and second selection images as a key and extracts the history information item including both the identification information of the first selection image and the identification information of the second selection image. As a result of the search, if the corresponding history information item is not found, the already-processed state determination unit 105 determines that the first and second selection images have not been processed. However, if the corresponding history information item is found, the already-processed state determination unit 105 determines that the first and second selection images have already been processed. Furthermore, the already-processed state determination unit 105 acquires the identification information of the resultant image of the image processing associated with the found history information item. Thereafter, the already-processed state determination unit 105 outputs, to the display control unit 106, the acquired identification information of the resultant image of image processing.

Note that as in the first embodiment, when the roles of the two medical images that are to undergo image processing are distinguished, the following determination may be made. That is, it may be determined whether the combination of the first and second selection images has already been processed in accordance with whether a combination of the identification information and the role information of each of the first and second selection images is included in the history information item. Thus, when selection is made so that the combination of images that are to undergo image processing matches the history information item but the role is different from in the history information item, the risk of wrong determination that the combination has already been processed is eliminated.

(S9080) (Displaying Warning Message and Selection UI)

In step S9080, the display control unit 106 displays a warning message stating that the selected pair consisting of the first and second selection images has already been processed and displays a UI for the user to select whether to still execute the image processing or display the result of image processing performed before.

Figure 10:
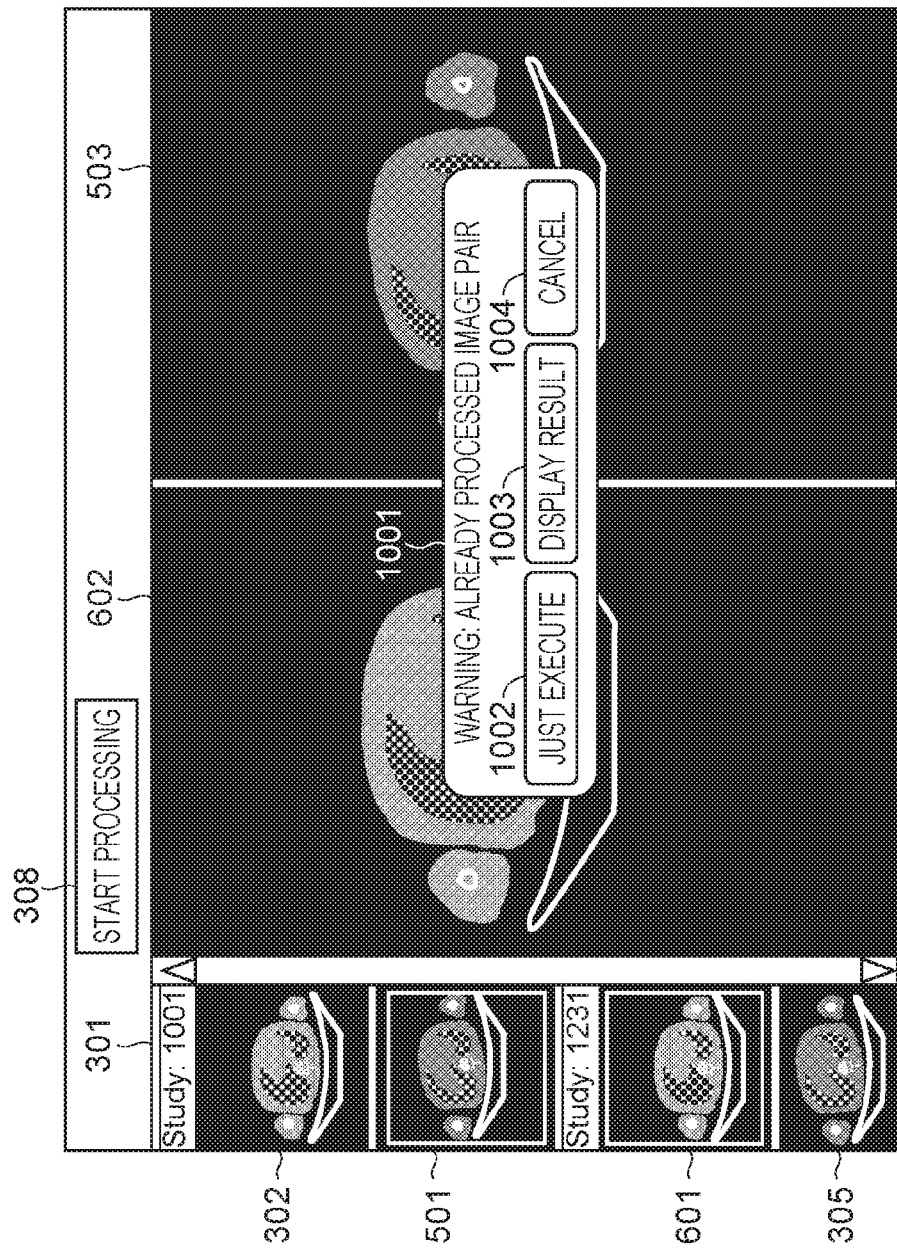
FIG. 10 is a diagram illustrating how a user can select whether to execute image processing or display the result when a processed image pair is selected.

FIG. 10 is a diagram illustrating how a user can select whether to execute image processing or display the result when a processed image pair is selected. "1001" represents a pop-up window including a warning message stating that the pair consisting of the selected first selection image 501 and second selection image 601 has already been processed and buttons for selecting one of still executing the image processing and displaying the result of image processing performed before. "1002" represents a button for selecting execution of image processing even though the image pair has already been processed, and "1003" represents a button for selecting display of the result of image processing performed before. "1004" represents a button for closing the pop-up window without displaying the result of image processing performed before. By displaying the pop-up window 1001, the user can easily get to know that the selected pair of images have already been processed and, at the same time, can easily display the result of image processing performed before. Note that the UI that enables the user to select whether to display the warning message or the result of image processing performed before is not limited thereto. In terms of the display of the warning message, the other example described for step S2090 may be applied. In addition, in terms of the UI that enables the user to select display of the result of image processing performed before, the UI may be disposed in a predetermined display area.

(S9090) (Is Image Processing Re-Execution Instruction Acquired?)

In step S9090, even when the processed image pair is selected, the display control unit 106 moves the process to step S9120 if an instruction to re-execute the image processing is acquired. However, if an instruction to re-execute the image processing is not acquired, the display control unit 106 moves the process to step S9100. More specifically, if the user presses a "just execute" button 1002, an image processing execution instruction is acquired. However, any one of the other buttons is pressed, the execution instruction is not acquired.

(S9100) (Is Instruction to Display Result Acquired?)

In step S9100, the display control unit 106 moves the process to step S9100 if the instruction to select display of the result of image processing performed before is acquired. However, the display control unit 106 moves the process to step S9020 if the instruction is not acquired. More specifically, if the user presses a "display result" button 1003, the instruction to select display of the result is acquired. However, if the user presses a cancel button 1004, the instruction to select display of the result is not acquired.

(S9110) (Reading Result of Image Processing Performed Before)

In step S9110, the display control unit 106 reads the result of image processing performed before which is stored in a database (not illustrated). More specifically, the display control unit 106 acquires, from a database (not illustrated), the resultant image of image processing that holds identification information corresponding to the identification information of the acquired resultant image of image processing.

As described above, the processing is performed by the information processing apparatus 100. As a result, in the case where the user selects the first and second selection images from the displayed examination list and instructs to start the processing, if the pair consisting of the first and second selection images is unprocessed, the information processing apparatus 100 normally performs the image processing and displays the image processing result. However, if the pair consisting of the first and second selection images has already been processed, the information processing apparatus 100 displays a warning message and a UI enabling the user to select whether to still perform the processing or display the result of the processing performed before. Subsequently, if the user instructs to still perform the image processing, the information processing apparatus 100 performs the image processing again on the already processed image pair and displays the resultant image of the image processing. However, if the user instructs to display the result of image processing performed before, the information processing apparatus 100 displays the image that is the result of image processing performed before. If no instruction is given, the processing returns again to the selection of a medical image to be processed.

According to the present embodiment, when a processed image pair is selected, the user can easily get to know that the image pair has already been processed and can easily examine the result of image processing performed before. Thus, the efficiency of examining the result of image processing can be improved. Furthermore, if, despite the existence of the already processed image pair, the user desires reprocessing, the image processing can be performed again and the result can be examined.

Modification 3-1

According to the third embodiment, the warning message and the UI for displaying the result of processing performed before are displayed only after the user instructs the start of the image processing with an image pair to be processed being selected. However, the time point of these displaying operations are not limited thereto. For example, when the first and second selection images are selected before step S9040, it may be determined whether the image pair has already been processed. If it is determined that the image pair has been processed, the warning message and the UI for displaying the result of processing performed before may be displayed. This process can be achieved as follows. That is, instead of performing step S9050 for acquiring the execution instruction of the image processing before the series of processes for displaying the warning message on the basis of the determination as to whether the image pair has already been processed (immediately before the step S9060), step S9050 is moved so as to be after the series of processes (immediately before step S9120). Thereafter, if the determination is No in step S9070, the processing proceeds to step S9050 that was moved. In this way, the user can easily get to know whether the image pair has already been processed when selecting the image pair, so that the user can more efficiently select an unprocessed medical image as a medical image to be processed.

Modification 3-2

According to the third embodiment, when a processed image pair is selected, both an instruction unit that acquires an instruction to execute image processing and an instruction unit that acquires an instruction to display a processed result are displayed. However, both the instruction units need not be displayed. For example, only the instruction unit that acquires the instruction to display the result of processing performed before may be displayed. This design can be implemented by removing the "display result" button 1003 in FIG. 10 and removing the process in step S9100. As described above, by removing the instruction unit that acquires the instruction to display the result, the number of options selected by the user can be reduced. Thus, the probability of the user providing a wrong instruction can be reduced.

Fourth Embodiment

According to the first and third embodiments, if the user specifies a pair of medical images that have already undergone image processing, a warning message is displayed. In contrast, according to the present embodiment, even if the user specifies a pair of medical images that have already undergone image processing, the image processing performed on the specified pair of medical images is disabled. As a result, the probability can be further reduced of regenerating the image already generated as the result of image processing by the user. Thus, waste can be eliminated. The processing according to the present embodiment is described below with reference to FIGS. 11 to 12. Note that the configuration of the information processing system according to the present embodiment is the same as that in FIG. 1 and, therefore, description of the information processing system is not repeated.

Figure 11:
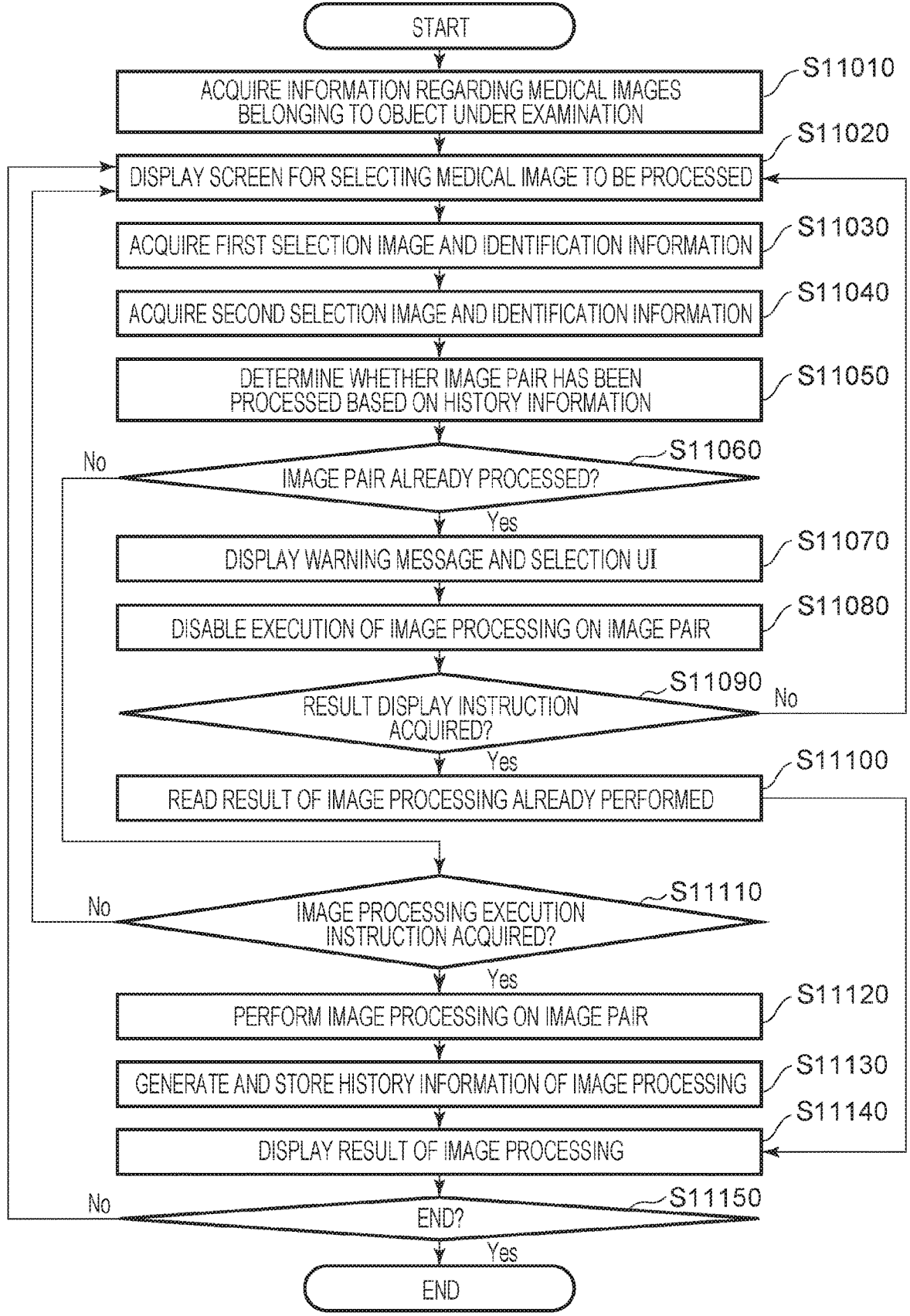
FIG. 11 is a flowchart illustrating the overall processing procedure according to a fourth embodiment.

FIG. 11 is a flowchart illustrating the overall processing procedure performed by the information processing apparatus 100. Note that in FIG. 11, steps S11010 to S11040, S11050, S11060, S11090, S11110, and S11120 to S11150 are the same as the following steps in the flowchart illustrated in FIG. 9. That is, the processes are the same as the processes in steps S9010 to S9040, S9060, S9070, S9110, and S9120 to S9150. Therefore, the description of the same processes is not repeated. Only the differences from the flowchart illustrated in FIG. 9 are described below.

(S11070) (Displaying Warning Message and Selection UI)

In step S11070, the display control unit 106 displays a warning message stating that the selected pair consisting of the first and second selection images has already been processed and a UI for selecting whether the result of image processing performed before is displayed. The display process in this step is the same as a process obtained by removing, from the process in step S9080 according to the third embodiment, the UI for acquiring the instruction to perform image processing again. Thus, description of the same portions as in step S9080 is not repeated.

Figure 12:
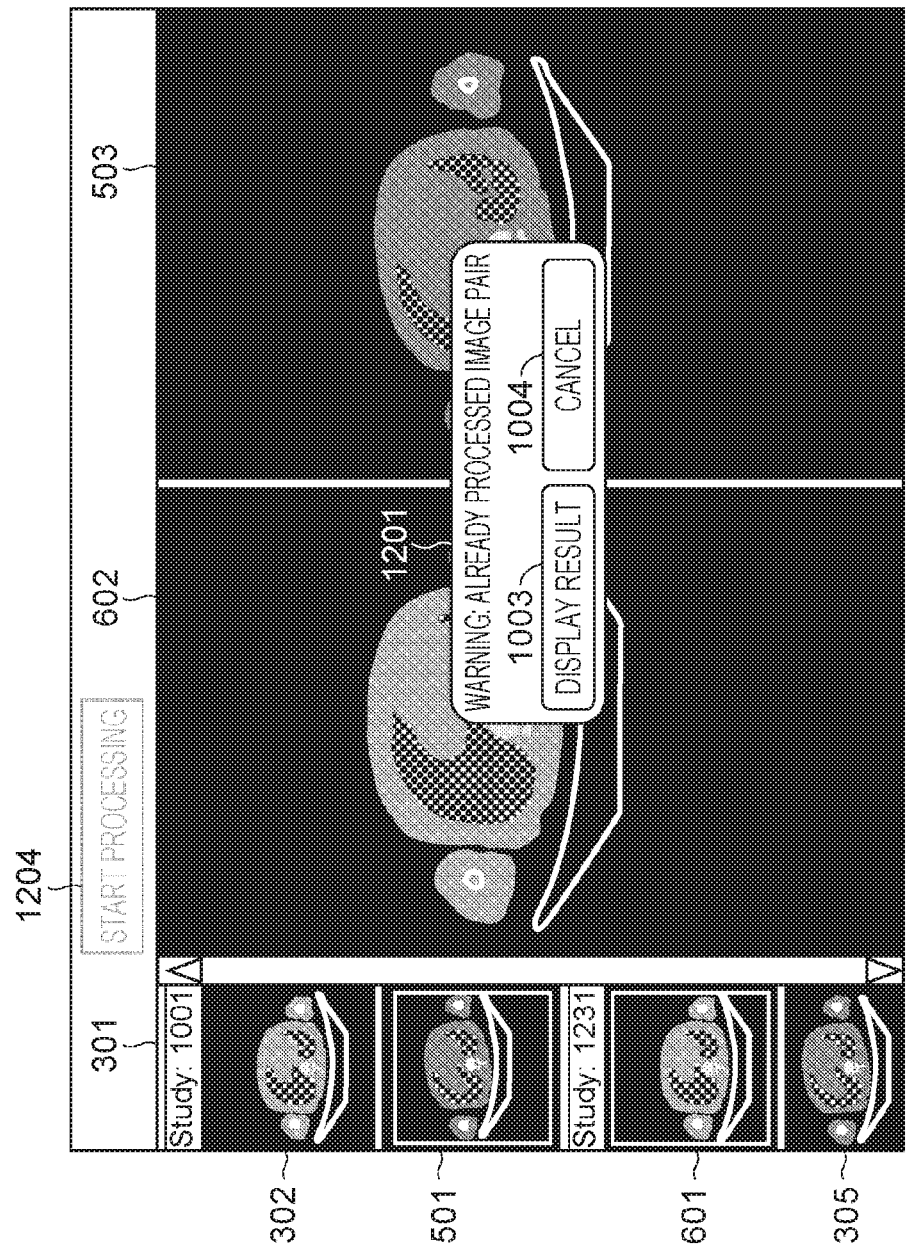
FIG. 12 is a diagram illustrating how the image processing is disabled when a processed image pair is selected.

FIG. 12 is a diagram illustrating how the image processing is disabled when a processed image pair is selected. "1201" represents a pop-up window including a warning message stating that the pair consisting of the selected first selection image 501 and second selection image 601 has already been processed and a button for selecting whether to display the result of image processing performed before. By displaying the pop-up window 1201, the same effect as that of the pop-up window 1001 illustrated in FIG. 10 can be obtained. However, unlike the pop-up window 1001, the pop-up window 1201 does not include a button for still executing the image processing. In this manner, the pop-up window 1201 disables the user to instruct re-execution of the image processing.

(S11080) (Disabling Execution of Image Processing on Image Pair)

In step S11080, the display control unit 106 disables execution of image processing on the selected pair of medical images (the first and second selected images) that has already been processed. More specifically, the display control unit 106 grays out a processing start button for instructing execution of image processing ("1204" in FIG. 12) to disable the button. This process can further reduce the probability of the user selecting an image that has already undergone image processing. Note that the technique for disabling the execution of image processing is not limited thereto. For example, by not displaying the processing start button 1204 itself, execution of image processing may be disabled. Alternatively, the processing start button 1204 may be highlighted instead of being grayed out or may remain unchanged. If one of the selected processed medical images in the pair (first and second images) is deselected, the grayed out processing start button returns to normal and, thus, the button is enabled.

As described above, the processing is performed by the information processing apparatus 100. Accordingly, in the case where the user selects the first and second selection images from the displayed examination list, if the pair consisting of the first and second selection images is unprocessed, the user can instruct the start of processing. Accordingly, if the user instructs the start of processing, the information processing apparatus 100 normally performs the image processing and displays the resultant image of the image processing. However, if the pair consisting of the first and second selection images has already been processed, the information processing apparatus 100 displays a warning message and a UI for selecting whether the result of the processing performed before is displayed. If the user instructs to display the result of image processing performed before, the information processing apparatus 100 displays the result of image processing performed before. However, if the user does not instruct to display the result, the processing returns again to the selection of the medical image to be processed.

According to the present embodiment, when the user selects a processed image pair, the user can easily get to know that the image pair has already been processed. In addition, the information processing apparatus 100 disables the user to instruct execution of the image processing. As a result, the probability can be reduced of regenerating the image already generated as the result of image processing by the user. Thus, waste can be eliminated.

Modification 4-1

According to the fourth embodiment, when a processed image pair is selected, a warning message stating that the image pair has already been processed is displayed. However, the image processing may be disabled without displaying the warning message. This design can be implemented by removing the processes in steps S11070, S11090, and S11100 and performing the process in step S11020 immediately after the process in step S11080 is performed. In this manner, upon selecting a processed image pair, the user is informed that the processed image is selected simply by disabling the processing start button 1204. Thus, the workflow of the user can be simplified. As a result, the user can efficiently select a medical image to be processed.

Modification 4-2

According to the fourth embodiment, when a processed image pair is selected, a warning message stating that the image pair has already been processed is displayed, and then a UI is displayed that prompts the user to specify display of the result of processing performed before. However, immediately after the processed image pair is selected, the result of processing performed before may be displayed without displaying the warning message. This design can be implemented by removing the processes in steps S11070 and S11090 and performing the process in step S11080 if determination in step S11060 is "Yes" and, thereafter, performing the process in step S11100 immediately after the process in step S11080 is performed. In this manner, upon selecting a processed image pair, the user can immediately examine the result of image processing performed on the selected image pair. Thus, the workflow of the user can be simplified. As a result, the user can efficiently examine the result of image processing.

According to the disclosure, unnecessary image processing is not performed again on a processed combination of images, and waste can be saved.

Other Embodiments

Embodiment(s) of the disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

The invention claimed is:
1. An information processing apparatus comprising:
   an acquisition unit configured to acquire history information of image processing on a combination of a plurality of medical images;
   a determination unit configured to determine, using the acquired history information, whether image processing has already been performed that is to be performed on at least one of candidate images that are candidates of a second medical image used for the image processing on combination with a first medical image selected by an operator; and an output unit configured to output a notification in accordance with a result of the determination, wherein the output unit outputs different notifications between i) in a case where a determination represents that the image processing has already been performed and ii) in a case where a determination represents that the image processing has not been performed.

2. The information processing apparatus according to claim 1, wherein the output unit causes a display unit to display information regarding the candidate images; and in that the output unit changes a display format of information regarding one or more of the candidate images that have undergone the image processing together with the first medical image and outputs the notification.

3. The information processing apparatus according to claim 2, wherein the information regarding the candidate images are thumbnail images indicating the candidate images or identification information indicating the candidate images.

4. The information processing apparatus according to claim 2, wherein the output unit displays the information regarding the candidate images on a GUI used by an operator to perform an operation to select the second medical image.

5. The information processing apparatus according to claim 1, wherein the first medical image is a reference image serving as a reference of image processing, and the second medical image is a comparison image to be compared with the reference image.

6. The information processing apparatus according to claim 1, wherein the history information includes identification information items each indicating a medical image used in image processing; and in that the determination unit makes the determination on the basis of whether the identification information items indicating the candidate images are included in the history information including the identification information item indicating the first medical image.

7. The information processing apparatus according to claim 6, wherein the history information further includes role information indicating the role of each of medical images used in image processing; and in that the determination unit makes the determination on the basis of whether the identification information items indicating the candidate images are included in the history information including the identification information item indicating the first medical image and the role information indicating the role of the selected first medical image.

8. The information processing apparatus according to claim 7, wherein the role is one of a role serving as a reference image that is a reference of image processing and a role serving as a comparison image to be compared with the reference image.

9. The information processing apparatus according to claim 7, wherein the history information further includes setting information used in image processing; and in that the determination unit further makes the determination on the basis of whether the setting information that is currently set for image processing is included in the history information including the identification information item indicating the first medical image.

10. The information processing apparatus according to claim 1, wherein if the selected first medical image is deselected, the output unit stops outputting the notification.

11. The information processing apparatus according to claim 1, further comprising:

a restriction unit configured to restrict selection of the second medical image from among the one or more candidate images determined to have already undergone image processing performed together with the first medical image.

12. The information processing apparatus according to claim 1, wherein the image processing is processing of calculating a difference between a plurality of medical images.

13. The information processing apparatus according to claim 1, wherein the output unit outputs notifications by changing a display form of information to be displayed on a display unit between i) in a case where a determination represents that the image processing has already been performed and ii) in a case where a determination represents that the image processing has not been performed.

14. A method for controlling an information processing apparatus, the method comprising:

acquiring history information of image processing on a combination of a plurality of medical images;

determining, using the acquired history information, whether image processing has already been performed that is to be performed on at least one of candidate images that are candidates of a second medical image used for the image processing on combination with a first medical image selected by an operator; and outputting a notification in accordance with a result of the determination;

wherein the outputting outputs different notifications between i) in a case where a determination represents that the image processing has already been performed and ii) in a case where a determination represents that the image processing has not been performed.

15. The method according to claim 14, wherein the outputting outputs notifications by changing a display form of information to be displayed on a display unit between i) in a case where a determination represents that the image processing has already been performed and ii) in a case where a determination represents that the image processing has not been performed.

16. A non-transitory computer-readable storage medium storing a computer program for causing a computer to execute a method for controlling an information processing apparatus, the method comprising:

acquiring history information of image processing on a combination of a plurality of medical images;

determining, using the acquired history information, whether image processing has already been performed that is to be performed on at least one of candidate images that are candidates of a second medical image used for the image processing on combination with a first medical image selected by an operator; and outputting a notification in accordance with a result of the determination;

wherein the outputting outputs different notifications between i) in a case where a determination represents that the image processing has already been performed and ii) in a case where a determination represents that the image processing has not been performed.

17. The non-transitory computer-readable storage medium according to claim 16, wherein the outputting outputs notifications by changing a display form of information to be displayed on a display unit between i) in a case where a determination represents that the image processing has already been performed and ii) in a case where a determination represents that the image processing has not been performed.

18. An information processing apparatus comprising:
an acquisition unit configured to acquire history information of image processing on a combination of a plurality of medical images;
a determination unit configured to determine, using the acquired history information, whether image processing has already been performed that is to be performed on at least one of candidate images that are candidates of a second medical image used for the image processing on combination with a first medical image; and
an output unit output the notification outputs a notification indicating that the image processing have been performed when a determination represents that the image processing has already been performed, and the output unit does not output the notification indicating that the image processing have been performed when a determination represents that the image processing has not been performed.

19. An information processing apparatus comprising:
an output unit causes a display unit to display information regarding a plurality of medical images;
an acquisition unit configured to acquire history information of image processing on a combination of a plurality of medical images;
a determination unit configured to determine, using the acquired history information, whether image processing has already been performed that is to be performed on at least one of candidate images that are candidates of a second medical image used for the image processing on combination with a first medical image selected by an operator,
wherein the output unit changes a display format of information regarding one or more of the candidate images that the image processing have been performed.

* * * * *